US009770585B2

(12) United States Patent
Ollivier

(10) Patent No.: US 9,770,585 B2
(45) Date of Patent: *Sep. 26, 2017

(54) RETRACTABLE SCREW INTRACARDIAC LEAD FOR CARDIAC STIMULATION AND/OR DEFIBRILLATION

(71) Applicant: SORIN CRM SAS, Clamart (FR)

(72) Inventor: Jean-François Ollivier, Gif sur Yvette (FR)

(73) Assignee: SORIN CRM SAS, Clamart (FR)

( * ) Notice: Subject to any disclaimer, the term of this patent is extended or adjusted under 35 U.S.C. 154(b) by 25 days.

This patent is subject to a terminal disclaimer.

(21) Appl. No.: 14/715,008

(22) Filed: May 18, 2015

(65) Prior Publication Data

US 2015/0246223 A1    Sep. 3, 2015

Related U.S. Application Data

(63) Continuation of application No. 12/768,588, filed on Apr. 27, 2010, now Pat. No. 9,037,265.

(51) Int. Cl.
  *A61N 1/00* (2006.01)
  *A61N 1/05* (2006.01)
  *A61N 1/04* (2006.01)

(52) U.S. Cl.
  CPC .......... *A61N 1/0573* (2013.01); *A61N 1/0472* (2013.01); *A61N 1/05* (2013.01); *A61N 1/057* (2013.01)

(58) Field of Classification Search
  None
  See application file for complete search history.

(56) References Cited

U.S. PATENT DOCUMENTS 4,106,512 A    8/1978   Bisping
4,953,564 A    9/1990   Berthelsen
(Continued)

FOREIGN PATENT DOCUMENTS

DE    37 12 082    10/1988
EP    0 591 053    4/1994
(Continued)

OTHER PUBLICATIONS

Preliminary Search Report for French Patent Application No. 0952766, dated Dec. 8, 2009, 2 pages.

*Primary Examiner* — Eric D Bertram
*Assistant Examiner* — Elizabeth K So
(74) *Attorney, Agent, or Firm* — Foley & Lardner LLP

(57) ABSTRACT

A retractable screw-type stimulation or defibrillation intracardiac lead is disclosed. According to one embodiment, the lead comprises a flexible hollow sheath (12) having at its distal end a lead head (10) and a connector (66) at its proximal end. The connector comprises a pin (62) connected to a lead head electrode (18). The lead head comprises a tubular body (28), at least one electrode (18, 20) for stimulation or defibrillation, a moving element translationally and rotationally moving within the tubular body in a helical motion, and an anchoring screw (24) axially moving with respect to the tubular body, and a deployment mechanism (22) to deploy the anchoring screw out of the tubular body (28). The lead is a co-radial type, and the moving element (26) secured to the anchoring screw is connected to the tubular body (28) by a helical guide (46) and a coupling finger (56) protruding between two successive turns of the helical guide (46) for transforming a rotary movement imparted to the lead body in a deployment or retraction movement of the moving element (26). The helical guide (46) is resiliently compressible, with a free end (52) with a flat area (54) facing a flange (38) in vis-à-vis, so as to pinch (Continued)

the coupling finger (56) and to perform the function of a clutch limiting the torque transmitted to the anchoring screw by the rotation of the lead body, even in case of continuation of this rotation.

20 Claims, 4 Drawing Sheets

(56) References Cited

U.S. PATENT DOCUMENTS

| | | |
|---|---|---|
| 5,447,534 A | 9/1995 | Jammet |
| 5,531,780 A | 7/1996 | Vachon |
| 5,571,157 A | 11/1996 | McConnell |
| 5,716,390 A | 2/1998 | Li |
| 5,837,006 A | 11/1998 | Ocel et al. |
| 7,096,071 B2 | 8/2006 | Ollivier et al. |
| 7,580,758 B2 | 8/2009 | Junge et al. |
| 8,548,605 B2 | 10/2013 | Ollivier |
| 2003/0167082 A1* | 9/2003 | Ollivier ............... A61N 1/0573 607/126 |
| 2004/0068299 A1 | 4/2004 | Laske et al. |

FOREIGN PATENT DOCUMENTS

| | | |
|---|---|---|
| EP | 1 331 021 | 7/2003 |
| EP | 1 754 507 | 2/2007 |
| EP | 1 774 986 | 4/2007 |
| WO | WO-2007/053065 | 5/2007 |

* cited by examiner

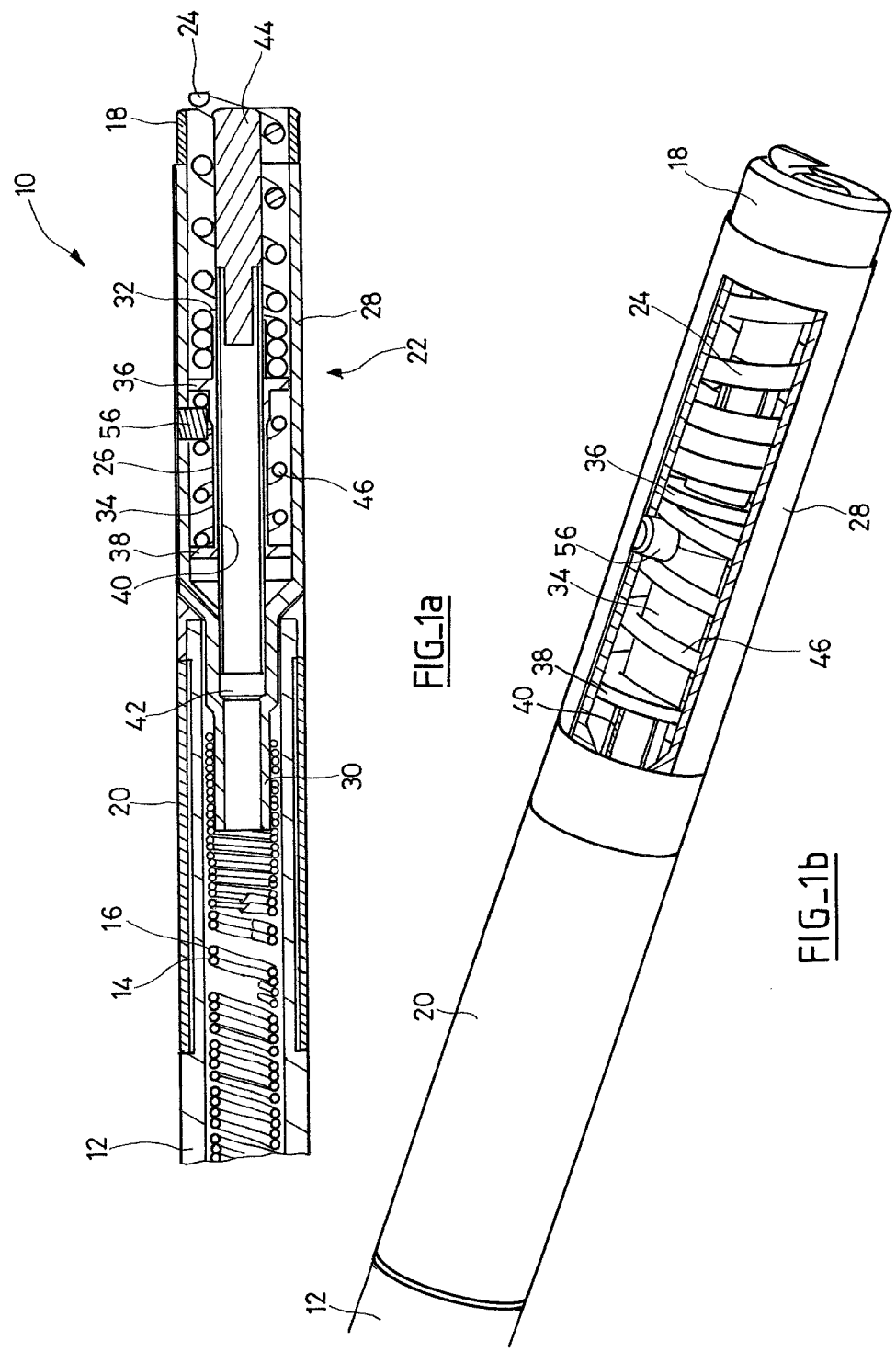

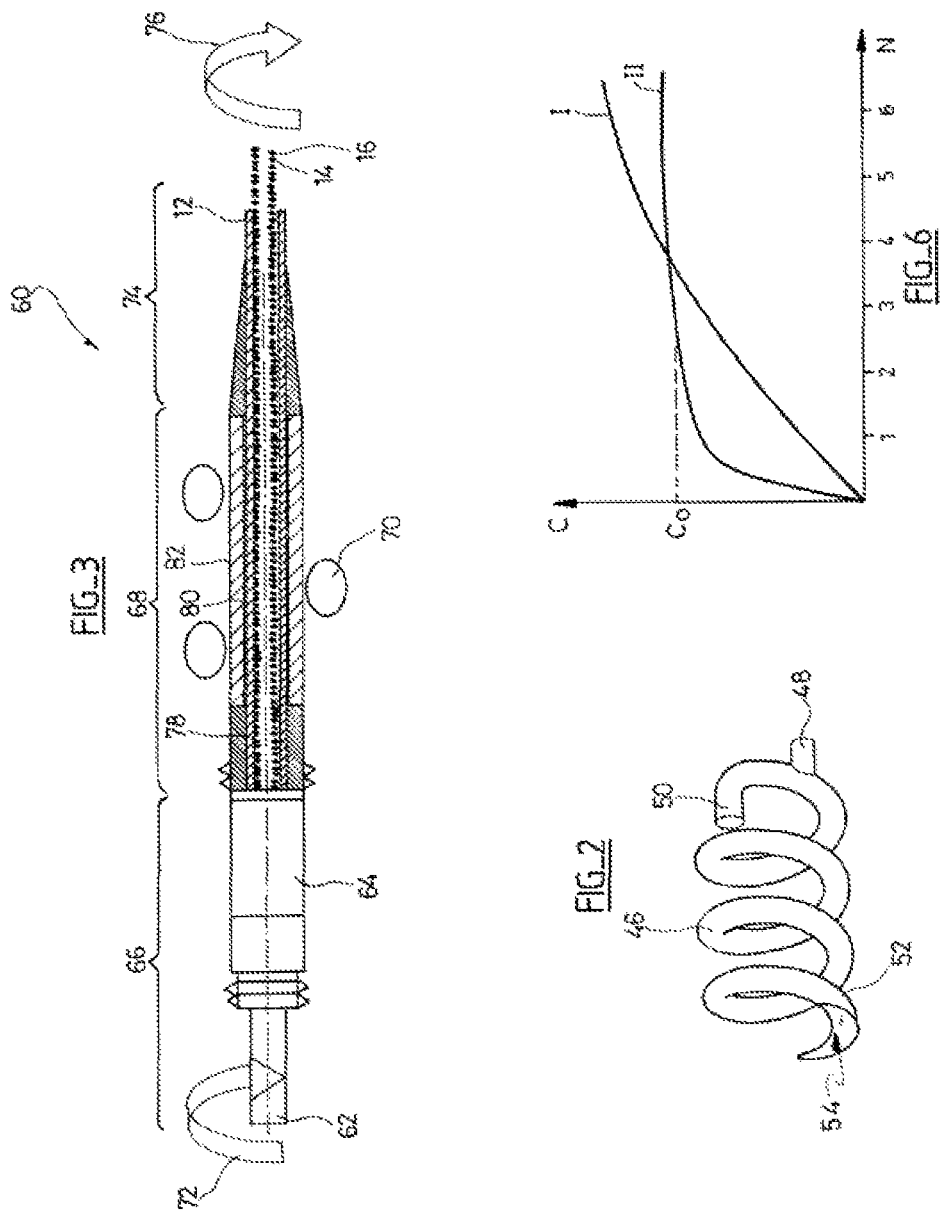

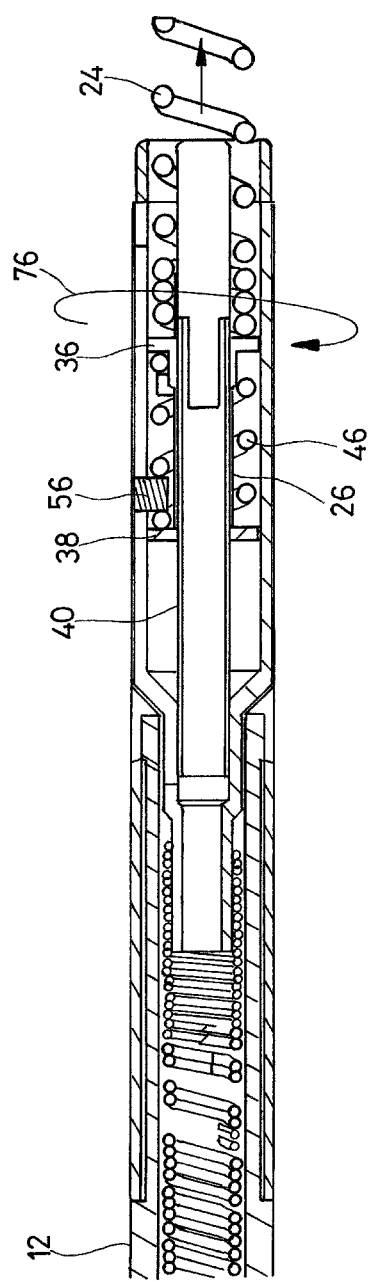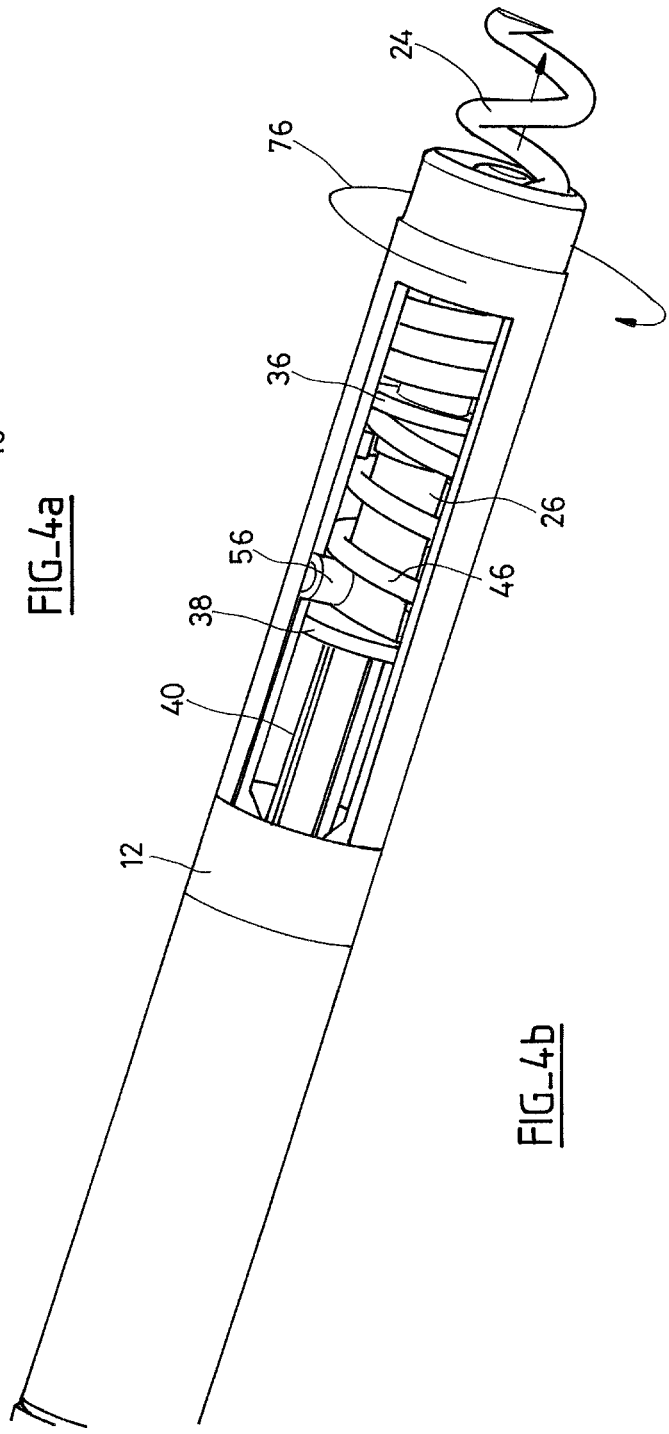
FIG_4a
FIG_4b

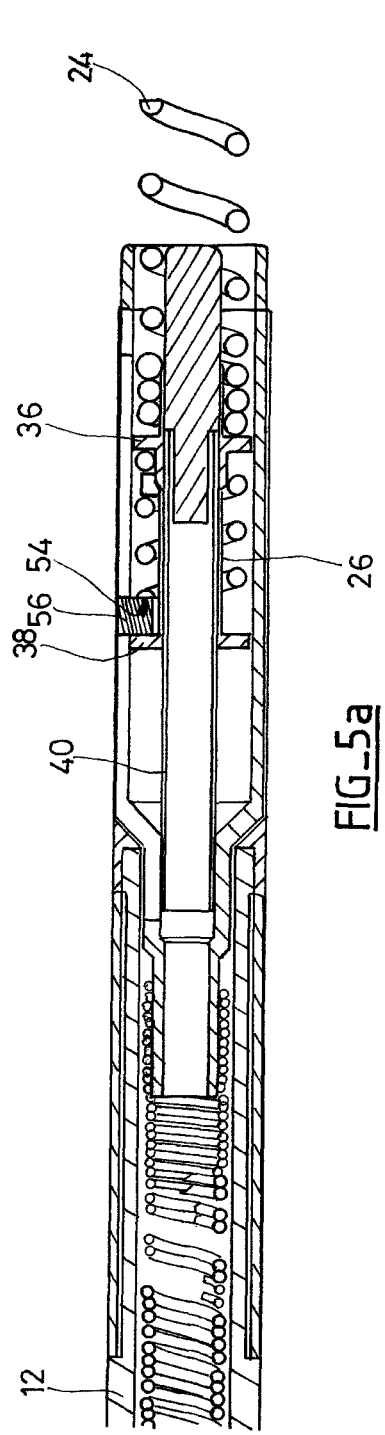
FIG_5a
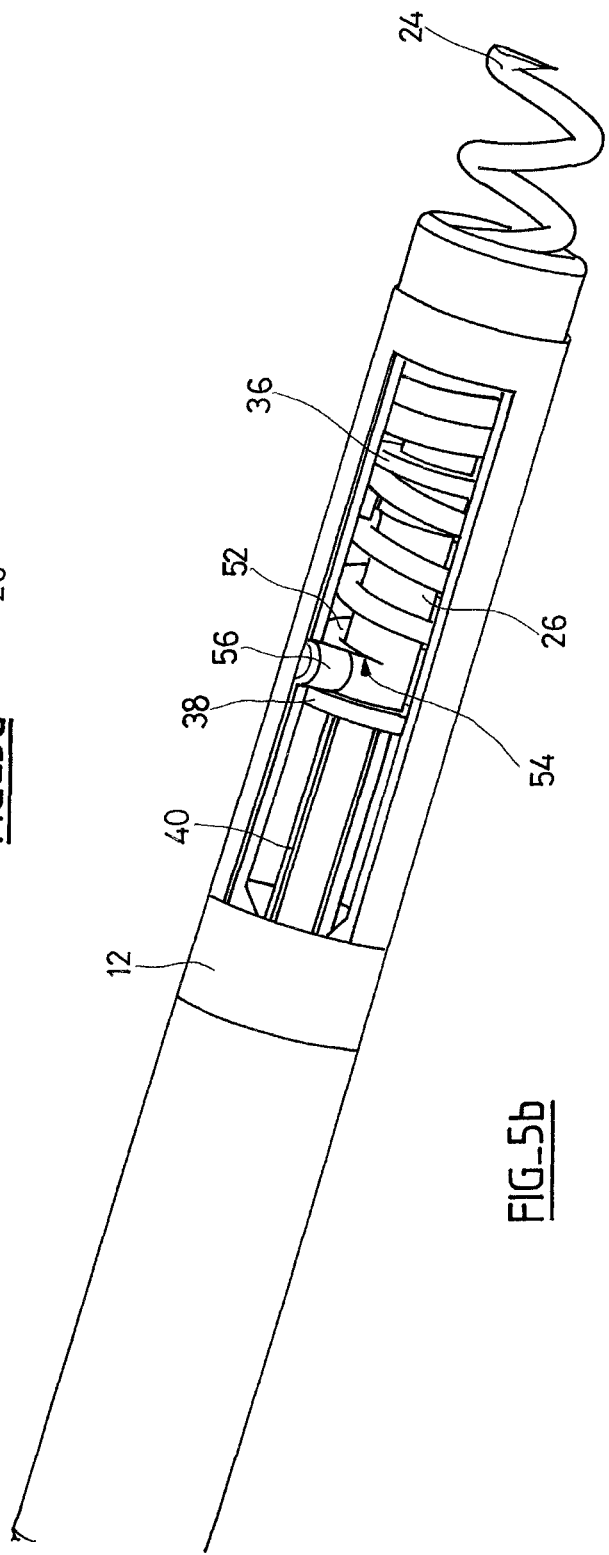
FIG_5b

RETRACTABLE SCREW INTRACARDIAC LEAD FOR CARDIAC STIMULATION AND/OR DEFIBRILLATION

CROSS-REFERENCE TO RELATED PATENT APPLICATIONS

This application is a continuation of U.S. application Ser. No. 12/768,588 (now U.S. Pat. No. 9,037,265), filed Apr. 27, 2010, which claims the benefit of and priority to French Patent Application No. 0952766, filed Apr. 28, 2009, both of which are hereby incorporated by reference herein in their entireties.

BACKGROUND

The present invention relates to intracardiac leads for pacing or defibrillation, and more particularly to such leads having a distal retractable screw allowing to anchor the leads at a desired contact point in the patient's endocardial tissue.

Intracardiac leads are implanted in a myocardium cavity of a patient and collect depolarization signals for continuously monitoring a patient's cardiac rhythm and, if necessary, for applying electrical stimulation, resynchronization, cardioversion and/or defibrillation pulses. These leads are coupled at the proximal end to an "active implantable medical device" as defined by Directive 90/385/EEC of 20 Jun. 1990 of the Council of European Communities.

Generally, a stimulation or defibrillation lead includes a "lead body" formed by a sheath or a tube (e.g., a flexible hollow tube). The lead body bears an electrode or electrodes that come into contact with the patient's myocardium, and a retractable screw. At its proximal end, the lead body is connected to a connection plug electrically connected to a connector header of a pacemaker or a defibrillator. The tube of the lead body contains one or more conductors electrically connecting the terminals of the proximal connection plug to the electrode or electrodes of the distal head.

For a lead body having a retractable screw, the lead head is equipped with a mechanism to retract the screw to protect the walls of the vein, and to avoid inadvertent hooking on the tricuspid valve or its Chordae tendineas during the introduction of the lead through the vein until the terminal end of the lead head comes to a stop against the wall of the endocardium. The retractable screw system also protects the screw from any deformation that would render it ineffective.

Once the desired position is reached, the surgeon manipulates the lead and anchors it via a simultaneous double movement of axial translation, first deploying the screw out of the housing of the lead head, and second rotating the screw to achieve its anchorage in the wall of the endocardium.

The lead is normally of a pin-driven type. The surgeon holds in one hand the proximal end of the lead body and turns with the other hand, directly or through the intermediary of a tool, a pin at the proximal end. Specifically, the pin is secured to an axial conductor extending within the lead body, and this conductor is free in rotation and is connected at its distal end to the deployment mechanism of the screw.

This technique assumes that the configuration of integrated conductors inside the lead body is of a "coaxial" type, for example, with a central conductor that is used to transfer the rotational torque to the mechanism for deploying the screw and a coaxial conductor extending around the periphery of, but interior to, the lead body.

A variant of this screw manipulation, different from rotating the pin connector, concerns using the end of a stylet inserted into the lead body, as described in EP 1 331 021 A1 and its US counterpart U.S. Pat. No. 7,096,071 (both assigned to ELA Medical, now known as Sorin CRM). This technique provides a limiting function for the drive torque of the screw by twisting the internal part of the stylet. The drive torque limitation allows in particular avoiding tissue and/or screw damage, in order to enable several attempts to anchor the lead if the electrical performance is deemed insufficient.

Another technique is proposed by EP 0 591 053 A1 and its US counterpart U.S. Pat. No. 5,447,534 (both assigned to ELA Medical, now known as Sorin CRM) which describe the Stelix™ brand lead currently marketed by Sorin CRM, Clamart, France. To deploy the screw, a surgeon inserts into the lead body a "stylet-screwdriver" type of stylet whose distal end has a flattened shape cooperating with a counterpart body of the screw deployment mechanism inside the lead head. The deployment is achieved by maintaining with one hand the stylet-screwdriver, and by turning with the other hand the lead body (the proximal portion of the sheath) over five to six complete turns. The lead head is equipped with a system to limit the drive torque that minimizes the torsion strain during screwing: if the resisting torque during screwing exceeds a given threshold, the screw is no longer driven by the rotation of lead body.

This system is effective, safe, and reversible. The surgeon can remove and retract the screw by an opposite maneuver to the installation procedure. However, the flexibility of deployment by rotating the lead body goes against the usual pin-driven maneuver which, as explained above, maintains the end of the lead body fixed and rotates the end of the connector pin (or the handle of a stylet emerging from the lead body in the same place).

Another drawback common to the above-described retractable screw devices, is their relatively large dimensions. The standard diameter of these intracardiac leads is about 7 French (1 French=⅓ mm), thus requiring the use of an 8-French introducer. The value of 7 French corresponds to a minimum technical limit with which it is difficult and dangerous to overcome with the "coaxial configuration" type leads described above. Indeed, for reliability, the lead body requires a minimum thickness of insulation and of conductor. Moreover, the retractable mechanism must also be technically manufacturable to keep an "isodiameter" type configuration, in which a lead having the same diameter along the length of the distal part to be implanted in the venous system, specifically to facilitate the implantation (and a subsequent explantation). This means that the outer surface of the lead, including the location of the electrodes and the deployment mechanism of the screw, is required to maintain its diameter with a tight tolerance. These constraints make it difficult to realize these leads, particularly because of the need for a reliable electrical connection between the inner and outer conductors and the corresponding electrodes of the lead head.

To reduce the diameter of the leads, a different configuration of the connecting conductors has been proposed, a configuration known under the names "co-radial" or "with insulated conductors". A lead realized according to this technology is described in U.S. Pat. No. 5,571,157. In this co-radial configuration, the two (or more) conductors are insulated conductors wound side by side in a region of the peripheral wall of the sheath of the lead body, forming a coil of single radius (hence the name "co-radial"), thus on a single layer, unlike the coaxial configurations involving two (or more) layers to integrate the different conductors. Insofar as all the conductors are arranged in a single layer, it is possible to reduce the standard diameter to 4.8 French, and the lead can be made with a 5-French introducer. This makes the lead as small as that of a monopolar lead, but with the functionalities of a bipolar or multipolar lead. A smaller diameter makes the lead more maneuverable in the venous system during its implementation, and a system with two or more leads can be implemented in a ventricle.

In order to equip such a co-radial lead with a deployable mechanism for fixing screws, the pin-driven maneuver technology is a priori not applicable. Indeed, it seems difficult to run one conductor over another (although this possibility is envisaged by the U.S. Pat. No. 5,716,390), due to the reliability constraints of the electrical connections at both ends of the lead. On the other hand, the limited capacity of wound conductors to transmit torque reduces the effectiveness for deploying the anchor screw.

SUMMARY OF THE INVENTION

It is, therefore, an object of the present invention to provide an improved bipolar or multipolar lead with a retractable anchoring screw.

The present invention proposes to that purpose a stimulation or defibrillation intracardiac lead having a deployable screw mechanism. The lead includes a flexible hollow sheath terminated at its distal end by a connector comprising at least one connection pin to an electrode of a lead head. The lead head comprises: an outer tubular body; at least one stimulation and/or defibrillation electrode; an anchoring screw inside the tubular body movable between a refracted position and a deployed position, said anchoring screw being mounted at the distal end of the moving element that is mobile in translation and rotation within the tubular body according to an helical movement; and a deployment mechanism. The deployment mechanism comprises a means for coupling the moving element to control the movement of the moving element from a retracted position toward a deployed position, and/or from the deployed position to the retracted position. The lead head rotates and simultaneously advances to penetrate into the endocardium wall of the anchoring screw. The lead further comprises at least one conducting wire extending along the entire length of the tubular body and connecting the electrode or a corresponding electrode, to the connection pin of the connector at the proximal end.

In a manner characteristic of the present invention, the conductor or conductors are preferably insulated conductors wound in a region of the peripheral wall of the tubular body in a co-radial type configuration. Further, the means for coupling the deployment mechanism preferably comprises means for coupling to the tubular body comprising an helical guide carried by the deployment mechanism. This helical guide is mobile in translation and in rotation within the tubular body transforms a rotational movement imparted to the tubular body by a rotation of the hollow sheath transmitted from the proximal end, in a movement of the deployment mechanism from the retracted position toward the deployed position, and vice versa.

In one embodiment, the sense of the pitch of the helical guide is preferably opposite to that of the anchoring screw. In another embodiment, the means for coupling comprises a coupling finger secured to the tubular body and projecting between two successive turns of the helical guide. Preferably, the deployment mechanism has two end flanges, and the helical guide is sandwiched between those two flanges. The helical guide optionally comprises a free end and an opposite end provided with means for securing to the flange placed in vis-à-vis. The helical guide is preferably a resiliently compressible element, configured so that during the movement of deployment, at the end position of the coupling finger, the reaction torque produced between the anchoring screw and the tubular body progressively causes a compression of the helical guide, then a disconnection of the coupling means, with consequently a limitation of the torque transmitted to the screw by the rotation of the tubular body, even in case of continuation of this rotation.

In yet another embodiment of the present invention, the helical guide comprises a free end having a flat area facing the flange placed in vis-à-vis, so as to pinch the coupling finger between the coupling flange and the flat area facing during the compression of the helical guide. The helical guide preferably comprises at its distal end a stop limiting the slide of the coupling finger along the helical guide. The lead head further comprises a central tube of axial guidance of the deployment mechanism, fixed in rotation to the tubular body and possibly comprising at its distal free end a cartridge to release an active ingredient at the anchoring point of the lead head.

Advantageously, the lead described herein has one or more of the following characteristics:
- a co-radial lead type deployment mechanism with a standard diameter of up to 4.8 French;
- a pin-driven maneuver-type deployment mechanism familiar to surgeons, preferably without any additional equipment;
- efficient transmission of torque, with a "1 for 1" type of response; a transmission providing an immediate response in one direction or another, without hysteresis, unlike conventional approaches involving an internal conductor as a transmitting element, which usually requires a rotation of four or five turns from the proximal end before getting a reaction at the distal end;
- protection against overscrewing (overtorque); if, for example, three or four turns are required for deploying and anchoring the screw, a higher number of turns has no effect, thanks to an automatic declutch system when the resisting torque on the anchoring screw exceeds a calibrated limit;
- easy removal of the lead by a maneuver reverse to the one performed for deploying and anchoring the lead;
- minimizing the length of the rigid distal part housing of the anchoring screw and its deployment mechanism to increase maneuverability in a venous system; the reduction of the size of the rigid part (typically to a length not exceeding 12 mm) allows better progression of the lead head during its introduction into the venous system; in addition, a long rigid distal part overflows into the atrium, thus is not satisfactory in a long term;
- high electrical performance, thanks to a small area of the distal stimulation electrode (typically not more than 2 $mm^2$, whereas with conventional coaxial configurations, this surface is rarely less than 4 $mm^2$) and a small distance between electrodes (typically not exceeding 10 mm);
- a fully iso-diameter configuration over the entire length of the lead including the distal housing, the anchoring screw and its deployment mechanism;
- presence of radio-opaque markers to control the deployment of the anchoring screw under fluoroscopy;
- possibility of "mapping", that is to say, finding an optimal position of the lead before the deployment of the screw under fluoroscopy, to find the optimal position with the best response to an electrical stimulation where the lead may be attached to the endocardium through the deployment of the anchoring screw, this mapping being done through (i) a definitive electrode (the lead), and/or (ii) with a definitive stimulation surface;

introduction of a guiding stylet into the lead body which come into abutment, distal, at a point closest to the tip of the lead head, so as to exert pressure on the location nearest possible to this end;

production from existing materials and proven techniques without an additional technological constraint "process".

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements.

FIGS. 1a and 1b illustrate a longitudinal section of an exemplary lead, according to one embodiment of the present invention in a configuration where the anchoring screw is in the retracted position;

FIG. 2 illustrates a helical guide of the deployment mechanism of the anchoring screw, according to one embodiment;

FIG. 3 illustrates an exemplary lead of the present invention at its proximal end, where the connector is located;

FIGS. 4a and 4b illustrate the lead of FIGS. 1a and 1b in a configuration where the anchoring screw is deployed;

FIGS. 5a and 5b illustrate the lead of FIGS. 4a and 4b in a configuration where the anchoring screw, fully deployed, is rotated by the lead body to be screwed into a tissue of the endocardium; and FIG. 6 is a diagram of the torque vs. number of turns for a lead of the prior art (I) and in accordance with the present invention (II).

DETAILED DESCRIPTION

With reference to the drawing, one will now describe several preferred embodiments of the present invention. In FIGS. 1a and 1b, lead head 10 having a retractable screw type lead is represented with anchoring screw 24 in the retracted position. Lead head 10 is mounted at the end of sheath 12. Sheath 12 has a shape of a hollow flexible tube incorporating two (or more) electrical conductors 14, 16 connected to respective electrodes 18, 20. A system of collinear double coil wires is shown, with two independent wires being connected to each electrode, for security reasons. Electrode 18 is a distal annular or tip electrode and electrode 20 is a proximal or ring electrode. Lead head 10 also includes deployment mechanism 22 for anchoring screw 24 in a wall of the endocardium, to ensure a mechanical connection with a myocardial tissue and to maximize the movement or dislodgement of lead head 10 once it is developed.

Anchoring screw 24 is secured to moving element 26 housed in tubular body 28 of lead head 10. Tubular body 28 is fixed to sheath 12, for example, by gluing, and ends in the rear by a tail 30 that is electrically and mechanically connected to conductor 14 to ensure electrical continuity from conductor 14 to distal electrode 18 located at the opposite end.

According to one embodiment, tubular body 28 is made of titanium and is externally coated with an insulating layer, for example, deposited with a parylene material. Anchoring screw 24 may also be preferably coated with an parylene insulating layer. Tubular body 28 made of titanium is radio-transparent, which allows monitoring the implementation of lead head 10 under fluoroscopy with radiopaque markers provided by electrodes 18 and 20 that are made of platinum-iridium radiopaque. The output radiopaque marker for the screw up position, according to a common technique, is defined by the two radiopaque masses formed by the distal electrodes 18 and by the package of contiguous coils forming the basis of anchoring screw 24 (also made of platinum-iridium), the two masses thus approaching each other when anchoring screw 24 advances.

Advantageously, electrode 18 has a reduced contact area, for example about 2 mm$^2$. The compactness of deployment mechanism 22 for the lead also reduces the inter-electrode distance between distal electrode 18 and proximal electrode 20, to a value of about 10 mm. The length of the rigid part of lead head 10 is also reduced to a value of about 12 mm for the length of tubular body 28. This reduced dimension facilitates the introduction and progress of a lead in a venous system. According to one embodiment, the overall diameter of lead head 10 is reduced to a value of 4.8 French, such that the implanted sheath 12 (isodiameter configuration) has a diameter of 5 French or smaller.

The structure of deployment mechanism 22 for anchoring screw 24 is as follows. Moving element 26 includes distal projection 32 on which anchoring screw 24 is rigidly fixed, for example, by welding. Anchoring screw 24 tracks the movements in translation and rotation of moving element 26. Central part 34 of moving element 26 has a tubular shape, bounded by two end flanges 36, 38 in the form of flat discs extending in respectively parallel radial planes.

Moving element 26 slides on axial guiding central tube 40 secured to its proximal region 42 with tubular body 28. Note that when a stylet guide is introduced into the lumen of the lead head 10, the end of the stylet abuts against the proximal region 42 of guiding tube 40. At the distal end, guiding tube 40 is advantageously provided with cartridge 44 of release of an active ingredient in the contact region of distal electrode 18 with a myocardium wall.

In central region 34 between flanges 36 and 38, moving element 26 carries helical guide 46, shown separately in FIG. 2. Helical guide 46 is made of a resilient material and is presented, for example, such as a helically wound wire over three to four turns in order to have a shape of a helical coil. The distal end (on the right in FIG. 2) of the helical guide 46 is secured to the mobile apparatus, for example, through a pin 48 axially oriented and extending in an homologous slot (not shown) of distal flange 36, or by laser welding to flange 36. To the distal end is also provided element 50 acting as a stop, for example, consisting of a return of the end of the cylindrical wire forming helical guide 46, axially directed and coming to intervene in the interval formed by the last turn of helical guide 46.

The opposite proximal end 52 of helical guide 46 is, unlike the distal end, a free end provided with flat area 54 extending in a plane substantially parallel to proximal flange 38. Helical guide 46 is compressed like a spring by a pressure exerted on its proximal free end 52.

Deployment mechanism 22 includes coupling finger 56 in the form of a cylindrical element, secured to the inside of tubular body 28 and radially directed. The size of coupling finger 56 is chosen so that it comes to be placed in the interval between two successive turns of helical guide 46, as shown in FIGS. 1a and 1b. The function of coupling finger 56 is to transform a rotational movement (absolute) imparted to lead body 10, and therefore to tubular body 28 to an axial translational movement of moving element 26 relative to tubular body 28 via helical guide 46. The translational motion of moving element 26 leads to the deployment of anchoring screw 24 out of tubular body 28. FIGS. 4a and 4b illustrate such a configuration where anchoring screw 24 is deployed.

FIG. 3 illustrates an exemplary proximal end 60 of the lead shown from the connector side. According to one embodiment, proximal end 60 is in the form of a standard connector, such as an IS-1 normalized connector, with two contacts 62, 64 connected to respective conductors 14, 16 incorporated into lead body 10. Contact 62 is preferably in the form of an axial pin, and is connected via conductor 14 to distal electrode 18 at the other end of the lead. Contact 64 is preferably a peripheral contact, connected via conductor 16 to proximal electrode 20 of lead head 10.

Region 66 carrying contacts 62, 64 is adjacent at its distal side by region 68 referred to as a back hood, which is dissociated in rotation from region 66. The back hood region 68 thus provides a region that can be held in one hand between fingers of a surgeon (fingers schematized with 70), while on the other hand the surgeon turns pin 62 to generate a rotational motion as indicated by arrow 72 directly or through an appropriate tool. This rotational motion is transmitted to the transitional motion of lead body 10 (arrow 76), and the tip region 74 extends beyond back hood region 68 throughout lead body 10 at the distal end. This is a classic pin-driven type maneuver allowing, by rotating pin 62, to impress on lead body 10 as a whole a rotation transmitted to lead head 10 at the other end. Back hood region 68, fixed during this rotation, allows the axial maintenance of the lead by the surgeon and ensures the accuracy of the rotational drive of pin 62. Back hood region 68 with a fixed grip area includes for this purpose on part 78 extending sheath 12 of lead body 10, sliding element 80 (e.g., a PTFE tube) provided with exterior coating 82, (e.g., silicone coating) to facilitate its handling by the fingers of the surgeon.

The surgeon performs the implantation of the lead in accordance with the present invention in the following manner. The implementation is based on the principle of using lead body 10 as a whole (including, particularly, the polyurethane insulation of the flexible sheath 12) to transmit the torque applied at the proximal end to the distal end, in the same method as for a fixed screw lead—but using the same procedure used for handling a pin-driven screw-type retractable lead. Advantageously, the implantation procedure by the surgeon is comparable to what was performed in a conventional implantation procedure, with the following steps:

implementation of a stylet, whether or not of a preformed shape, in the internal lumen of lead body 10;

introduction of the lead to a desired cardiac cavity through a venous system;

optional use of a tool for manipulating pin 62 of the connector;

maintenance with one hand on back hood region 68 of the connector placement of the lead tip against a heart wall and "anchoring" of anchoring screw 24, the slightly protruding portion of anchoring screw 24 (about 0.3 mm) coming to sting a myocardial tissue and stop rotating the lead. At this stage, the surgeon may make a mapping to assess the response from the myocardial tissue before drilling the screw fully into the myocardial tissue;

clockwise rotation of pin 62 advancing anchoring screw 24 and screwing it into the wall of the endocardium;

retreat of the stylet; and test of the fixation, for example, by a gentle traction.

Deployment mechanism 22 works in the following steps. Once the harpooning of anchoring screw 24 with a possible mapping by distal electrode 18 is completed (note that the mapping is performed with a final electrode and with a final stimulation surface, and therefore in the best conditions for the choice of best site of stimulation), anchoring screw 24 is locked in rotation. The clockwise rotation of lead body 10 induces, in response, the axial translation toward the front of moving element 26 via coupling finger 56 and helical guide 46, whose pitch is inverted compared to anchoring screw 24 and which slides on coupling finger 56. Anchoring screw 24 emerges gradually from the housing, until the coupling finger 56 reaches the end of helical guide 46, in a configuration illustrated in FIGS. 4a and 4b.

The continued rotation of lead body 10, and thus of coupling finger 56, starts to compress helical guide 46 due to its elasticity. Coupling finger 56 is blocked in the "vise" formed between flat area 54 and proximal flange 38 located vis-à-vis. This configuration of a "clutch" system is illustrated in FIGS. 5a and 5b.

Moving element 26 and anchoring screw 24 are temporarily attached by this clutch type connection, and through helical guide 46, to coupling finger 56 and lead body 10. The deployed anchoring screw 24 follows in rotation the rotational movement of lead body that the surgeon continues to give to the proximal end.

The continued rotation of lead body 10 causes screwing of anchoring screw 24 in a myocardial tissue, until stimulation element 18 comes into contact with the wall of an endocardium. This contact produces by reaction on anchoring screw 24 an increased resisting torque, said torque being transmitted to the clutch system. When this torque exceeds a calibrated limit by the compression of helical guide 46, coupling finger 56 frees from the clutch vise. Any further rotation of lead body 10 reproduces the same phenomenon. Consequently, there is no risk of damaging the tissue or even perforating the wall by excessive screwing (e.g., no risk of "carotage").

FIG. 6 illustrates the characteristic of torque transmitted by lead body 10 according to the number of turns (N) given to pin 62 for a conventional prior art lead (feature I) and for the lead of the present invention (feature II). Note the efficient transmission of torque by lead body 10 (especially the conductors and the polyurethane insulation) and by deployment mechanism 22, with an almost "one to one" response. The coupling reaches quickly a saturated value $C_0$ (feature II), unlike conventional leads involving an inner conductor as a transmission element for which it is necessary to give multiple revolutions of the pin before experiencing a response (feature I).

According to one embodiment, the clutch system of the present invention is calibrated to a coupling value of $C_0$ of about 0.05 to 0.20 N·cm. This ensures safety and provides a high tolerance on the number of turns to make a reliable and proper fixation. Even if three or four turns are sufficient, there is no contraindication if the surgeon wants to do ten, twenty or even thirty turns. The surgeon feels no resistance after the sufficient turns and thereafter simply feels on each declutch a clicking confirming that the anchoring screw has been deployed and screwed into the myocardial tissue. This maneuver is also achieved without any change in habits related to the use of traditional leads.

A reverse rotation of the lead body 10 produces the clutch of coupling finger 56 in the coils of helical guide 46. Coupling finger 56 follows the turns until it comes up against body 50 of movement limitation (FIG. 2) ensuring the rotation coupling of lead body 10 and of anchoring screw 24. The continuation of this rotation in reverse sense has the effect of unscrewing anchoring screw 24 from the myocardial tissue. At the end of the maneuver, the assembly is ready for a repositioning, after the surgeon slightly pulled the lead to ensure that it is detached from the wall.

One skilled in the art will appreciate that the present invention can be practiced by embodiments other than those described herein, which are provided for purposes of illustration and not of limitation.

What is claimed is:

1. A method of implanting a lead at a target stimulation site, the method comprising:
   providing a lead comprising a sheath and a body coupled to a distal end of the sheath, wherein the sheath is configured to rotate under a rotary force applied to a proximal end of the lead;
   positioning a distal end of the lead at the target stimulation site;
   imparting a rotational force at the proximal end of the lead, wherein the rotational force is transmitted by the sheath to the body at the distal end of the lead, and further wherein imparting the rotational force causes a moving element comprising a guide contained within the body to move translationally along the body via interaction with a coupling finger that extends radially inward from the body, thereby translationally deploying an anchoring screw carried by the moving element without imparting rotational movement to the anchoring screw;
   engaging the guide of the moving element and the coupling finger of the body by imparting the rotational force until the moving element reaches a fully deployed position; and
   continuing to impart a rotational force at the proximal end of the lead when the guide of the moving element and the coupling finger of the body are engaged, thereby causing a rotational movement of the anchoring screw to fix the screw to the target stimulation site.

2. The method of claim 1,
   wherein imparting the rotational force at the proximal end of the lead, prior to engaging the moving element and the body, causes the coupling finger to interact with and move along the helical guide of the moving element to translationally move the moving element.

3. The method of claim 1, wherein the coupling finger is secured to the body and placed in an interval between two successive turns of the helical guide.

4. The method of claim 1, wherein engaging the moving element and the body comprises engaging the coupling finger with an end portion of the helical guide.

5. The method of claim 1, wherein the moving element comprises a flange extending radially from an axis of the moving element, and wherein the flange acts on the anchoring screw to deploy the anchoring screw.

6. The method of claim 5, wherein the helical guide is a compressible element.

7. The method of claim 6, further comprising:
   compressing the helical guide upon engaging the moving element and the body;
   producing a reaction torque between the anchoring screw and the body causing a progressive compression of the helical guide; and
   continuing to impart the rotational force causing a torque to reach a threshold value, thereby causing a declutch of the helical guide and the coupling finger to limit the torque transmitted to the anchoring screw by the rotation of the body.

8. The method of claim 7, further comprising pinching the coupling finger between a flat area on the helical guide and the flange during the compression of the helical guide.

9. The method of claim 1, further comprising providing the body with an axial guiding tube for axial guidance of the moving element.

10. The method of claim 9, wherein the axial guiding tube is rotationally coupled to the body.

11. The method of claim 10, further comprising releasing an active ingredient to the target stimulation site from a cartridge at a distal end of the axial guiding tube.

12. The method of claim 1, wherein the helical guide has a first pitch and the anchoring screw has a second pitch that is reverse to that of the first pitch.

13. A method of implanting a lead at a target stimulation site, the method comprising:
   providing a lead comprising a sheath and a body coupled to a distal end of the sheath, wherein the sheath is configured to rotate under a rotary force applied to a proximal end of the lead, wherein the moving element comprises a helical guide carried by the moving element, and wherein the body comprises a coupling finger extending radially inward from the body;
   positioning a distal end of the lead at the target stimulation site;
   imparting a rotational force at the proximal end of the lead, wherein the rotational force is transmitted by the sheath to the body at the distal end of the lead, and further wherein imparting the rotational force causes the moving element contained within the body to move translationally along the body via interaction with the coupling finger of the body, thereby translationally deploying an anchoring screw carried by the moving element without imparting rotational movement to the anchoring screw;
   engaging the helical guide of the moving element to the coupling finger of the body by compressing the helical guide and securing the coupling finger in the helical guide when the moving element reaches a fully deployed position; and
   continuing to impart a rotational force at the proximal end of the lead when the helical guide of the moving element and the coupling finger of the body are engaged, thereby causing a rotational movement of the anchoring screw to fix the screw to the target stimulation site.

14. The method of claim 13, wherein the coupling finger is secured to the body and placed in an interval between two successive turns of the helical guide.

15. The method of claim 13, wherein engaging the moving element and the body comprises engaging the coupling finger with an end portion of the helical guide.

16. The method of claim 13, wherein the moving element comprises a flange extending radially from an axis of the moving element, and wherein the flange acts on the anchoring screw to deploy the anchoring screw.

17. The method of claim 13, further comprising:
   producing a reaction torque between the anchoring screw and the body caused by a progressive compression of the helical guide; and
   continuing to impart the rotational force causing a torque to reach a threshold value, thereby causing a declutch of the helical guide and the coupling finger to limit the torque transmitted to the anchoring screw by the rotation of the body.

18. The method of claim 13, further comprising pinching the coupling finger between a flat area on the helical guide and the flange during the compression of the helical guide.

19. The method of claim 13, wherein the helical guide has a first pitch and the anchoring screw has a second pitch that is reverse to that of the first pitch.

20. A method of implanting a lead at a target stimulation site, the method comprising:
- providing a lead comprising a sheath and a body coupled to a distal end of the sheath, wherein the sheath is configured to rotate under a rotary force applied to a proximal end of the lead, wherein the moving element comprises a helical guide carried by the moving element, and wherein the body comprises a coupling finger extending radially inward from the body;
- positioning a distal end of the lead at the target stimulation site;
- imparting a rotational force at the proximal end of the lead, wherein the rotational force is transmitted by the sheath to the body at the distal end of the lead, and further wherein imparting the rotational force causes the moving element contained within the body to move translationally along the body via interaction with the coupling finger of the body, thereby translationally deploying an anchoring screw carried by the moving element without imparting rotational movement to the anchoring screw;
- engaging the helical guide of the moving element and the coupling finger of the body by imparting the rotational force until the moving element reaches a fully deployed position;
- continuing to impart a rotational force at the proximal end of the lead when the helical guide of the moving element and the coupling finger of the body are engaged, thereby causing a rotational movement of the anchoring screw to fix the screw to the target stimulation site;
- producing a reaction torque between the anchoring screw and the body causing a progressive compression of the helical guide; and
- continuing to impart the rotational force causing a torque to reach a threshold value, thereby causing a declutch of the helical guide and the coupling finger to limit the torque transmitted to the anchoring screw by the rotation of the body.

* * * * *